(12) United States Patent
Cramer et al.

(10) Patent No.: US 8,705,007 B2
(45) Date of Patent: Apr. 22, 2014

(54) INSPECTION APPARATUS, LITHOGRAPHIC APPARATUS, LITHOGRAPHIC PROCESSING CELL AND INSPECTION METHOD

(75) Inventors: Hugo Augustinus Joseph Cramer, Eindhoven (NL); Antoine Gaston Marie Kiers, Veldhoven (NL); Henricus Petrus Maria Pellemans, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 524 days.

(21) Appl. No.: 12/690,221

(22) Filed: Jan. 20, 2010

(65) Prior Publication Data

US 2010/0201963 A1   Aug. 12, 2010

Related U.S. Application Data

(60) Provisional application No. 61/151,665, filed on Feb. 11, 2009.

(51) Int. Cl.
| | |
|---|---|
| *G01B 11/00* | (2006.01) |
| *G01N 21/86* | (2006.01) |
| *G03B 27/32* | (2006.01) |
| *G03B 27/42* | (2006.01) |
| *G03B 27/74* | (2006.01) |

(52) U.S. Cl.
USPC ............ 355/68; 250/559.04; 355/53; 355/77; 356/399; 356/400; 356/401

(58) Field of Classification Search
USPC ............... 250/559.04–559.08, 559.29–559.3, 250/559.44, 492.2; 355/53, 55, 67–68, 71, 355/77; 356/302–305, 364–370, 399–401, 356/614–616, 624; 430/22, 30
See application file for complete search history.

(56) References Cited

U.S. PATENT DOCUMENTS 5,774,222 A   6/1998   Maeda et al.
(Continued)

FOREIGN PATENT DOCUMENTS

| CN | 1534271 A | 10/2004 |
|---|---|---|
| EP | 1 628 164 A | 2/2006 |
| JP | 08-162511 A | 6/1996 |
| KR | 10-2009-0013733 A | 2/2009 |

OTHER PUBLICATIONS

English-Language Abstract for Chinese Patent Publication No. 1534271 A, published Oct. 6, 2004, from the State Intellectual Property Office of the People's Republic of China; 1 page.

(Continued)

*Primary Examiner* — Toan Ton
*Assistant Examiner* — Colin Kreutzer
(74) *Attorney, Agent, or Firm* — Sterne, Kessler, Goldstein & Fox P.L.L.C.

(57) ABSTRACT

For angular resolved spectrometry a radiation beam is used having an illumination profile having four quadrants is used. The first and third quadrants are illuminated whereas the second and fourth quadrants aren't illuminated. The resulting pupil plane is thus also divided into four quadrants with only the zeroth order diffraction pattern appearing in the first and third quadrants and only the first order diffraction pattern appearing in the second and third quadrants.

27 Claims, 6 Drawing Sheets

(56) References Cited

U.S. PATENT DOCUMENTS

| | | | |
|---|---|---|---|
| 7,112,813 B2 | 9/2006 | Den Boef et al. | |
| 7,460,237 B1 | 12/2008 | Cramer | |
| 2003/0223630 A1* | 12/2003 | Adel et al. | 382/145 |
| 2006/0285111 A1 | 12/2006 | Raymond et al. | |
| 2008/0239265 A1* | 10/2008 | Den Boef | 355/53 |
| 2011/0027704 A1* | 2/2011 | Cramer et al. | 430/30 |
| 2011/0102753 A1* | 5/2011 | Van De Kerkhof et al. | 355/27 |
| 2012/0013881 A1* | 1/2012 | Den Boef et al. | 355/67 |
| 2012/0033193 A1* | 2/2012 | Van Der Schaar et al. | 355/67 |

OTHER PUBLICATIONS

English-Language Translation of the First Office Action directed to related Chinese Patent Application No. 201010116824.7, mailed Jul. 26, 2011, from the State Intellectual Property Office of the People's Republic of China; 3 pages.

English translation of Korean notification of Reasons for Refusal directed to related Korean Application No. 10-2010-0012423, Korean Intellectual Property Office, dated Apr. 29, 2011; 8 pages.

Extended European Search Report mailed May 7, 2010 for European Application No. 10151257.2-1226, 3 pgs.

* cited by examiner

INSPECTION APPARATUS, LITHOGRAPHIC APPARATUS, LITHOGRAPHIC PROCESSING CELL AND INSPECTION METHOD

CROSS REFERENCE TO RELATED APPLICATIONS

This application claims priority under 35 U.S.C. §119(e) to U.S. Provisional Patent Application No. 61/151,665, filed Feb. 11, 2009, which is incorporated by reference herein in its entirety.

BACKGROUND

1. Field of the Invention

The present invention relates to methods of inspection usable, for example, in the manufacture of devices by lithographic techniques and to methods of manufacturing devices using lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

In angular resolved spectrometry, a periodic mark on a substrate is simultaneously illuminated at various angles. The light diffracted by this mark is used to measure particular characteristics of that mark. If the period of the mark is sufficiently large, the diffracted light will contain higher diffraction orders. However, part of the first diffraction order is often mixed with part of the zeroth diffraction order, as shown in accompanying FIG. 5. This overlap of diffraction orders generally yields a less robust reconstruction of the characteristics of the mark. In order to separate out the different diffraction orders annular illumination can be used, and this results in separated zeroth and first order diffraction patterns as shown in FIG. 6. However, it has been found that the use of such annular illumination may lead to errors in the measured mark characteristics since annular illumination provides less information in the diffracted light. For example, in annular illumination, there are no light beams near normal incidence that also contain information that is valuable for measuring the mark characteristics.

SUMMARY

It is desirable to provide a method of illuminating a substrate in which it is possible to separate the first and zeroth diffraction orders while at the same time illuminating the substrate with all possible angles of incidence and azimuthal angles. According to an aspect of the invention, there is provided an inspection apparatus configured to measure a property of a substrate. The apparatus comprises an illumination system configured to provide a beam of radiation; a radiation projector configured to project the radiation onto the substrate; a high numerical aperture lens; and a detector. The detector is configured to detect the radiation beam reflected from a surface of the substrate, and separately detects a zeroth and a first diffraction order. A resulting illumination profile of the beam of radiation projected by the radiation projector is such that the intensity distribution of the radiation beam is not symmetric about an imaginary line in a pupil plane and passing through the optical axis of the radiation projector.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 7A:
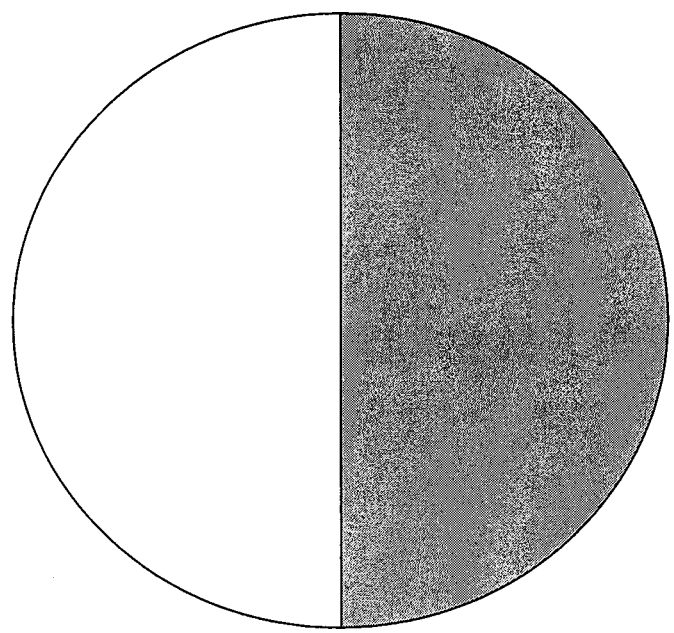

FIG. 7*a* depicts an illumination profile according to an embodiment of the invention.

Figure 7B:
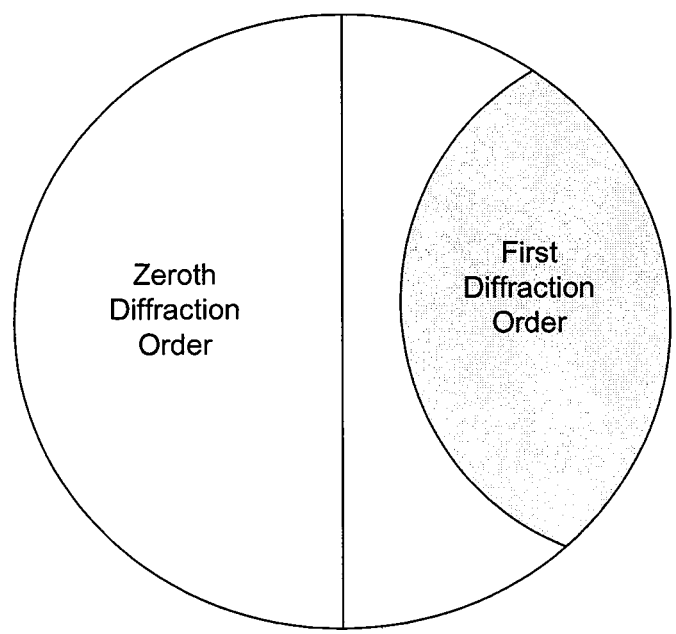

FIG. 7*b* depicts a pupil plane using the illumination profile depicted in FIG. 7*a*.

Figure 8A:
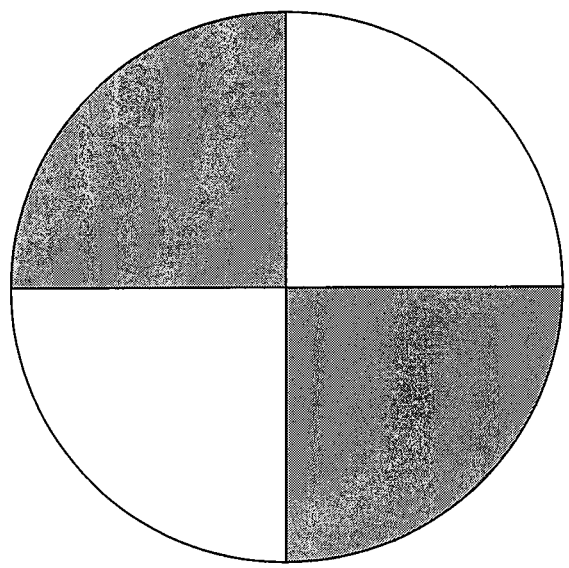

FIG. 8*a* depicts an illumination profile according to another embodiment of the invention.

Figure 8B:
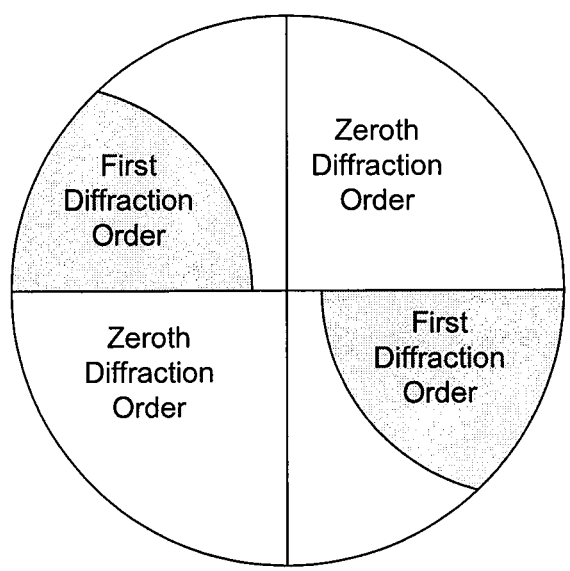

FIG. 8b depicts a pupil plane using the illumination profile depicted in FIG. 8a.

Figure 9A:
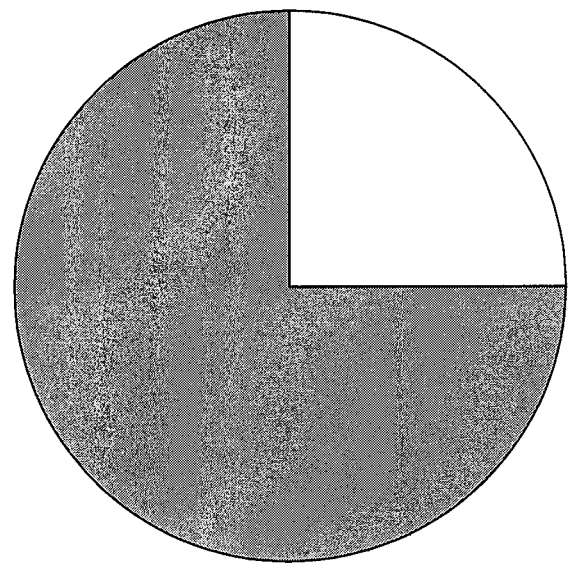

FIG. 9a depicts an alternative illumination profile.

Figure 9B:
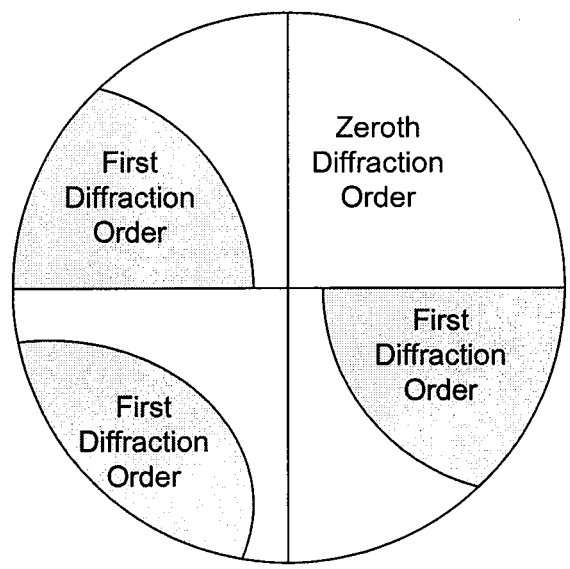

FIG. 9b depicts a pupil plane using the illumination profile depicted in FIG. 9a.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
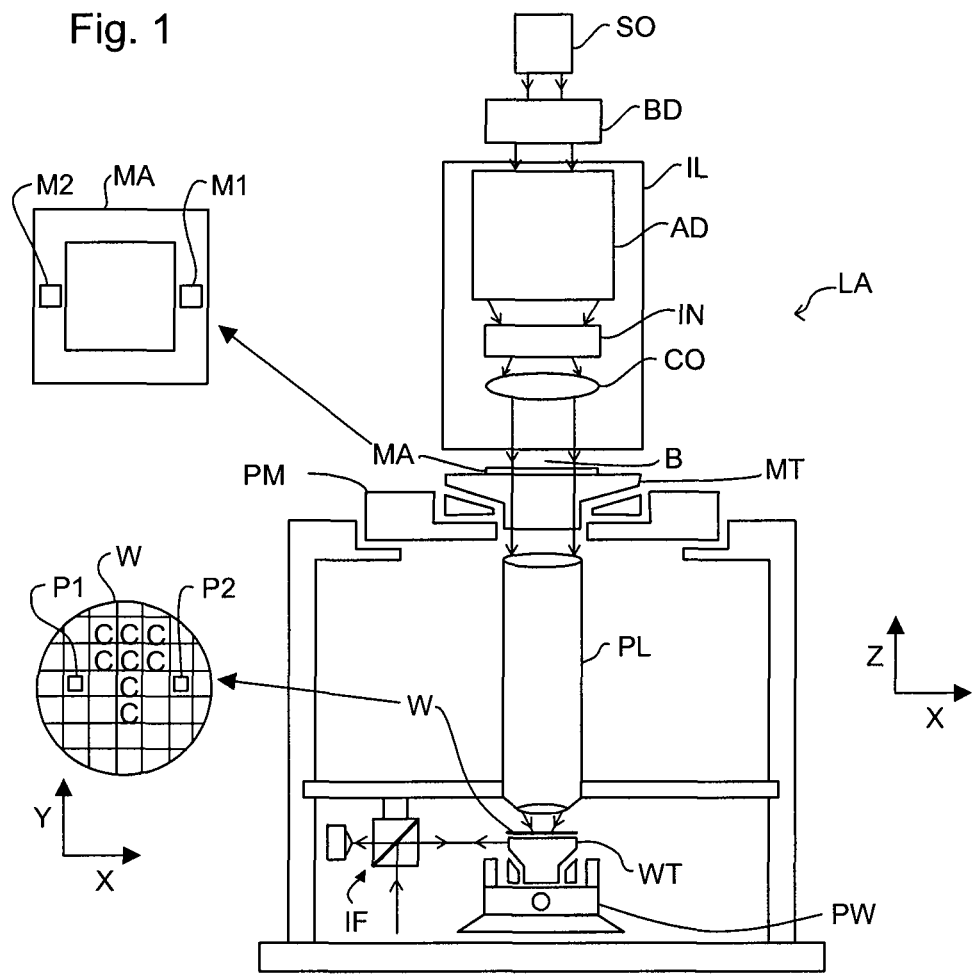
FIG. 1 depicts a lithographic apparatus.

FIG. 1 schematically depicts a lithographic apparatus. The apparatus comprises an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion 3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
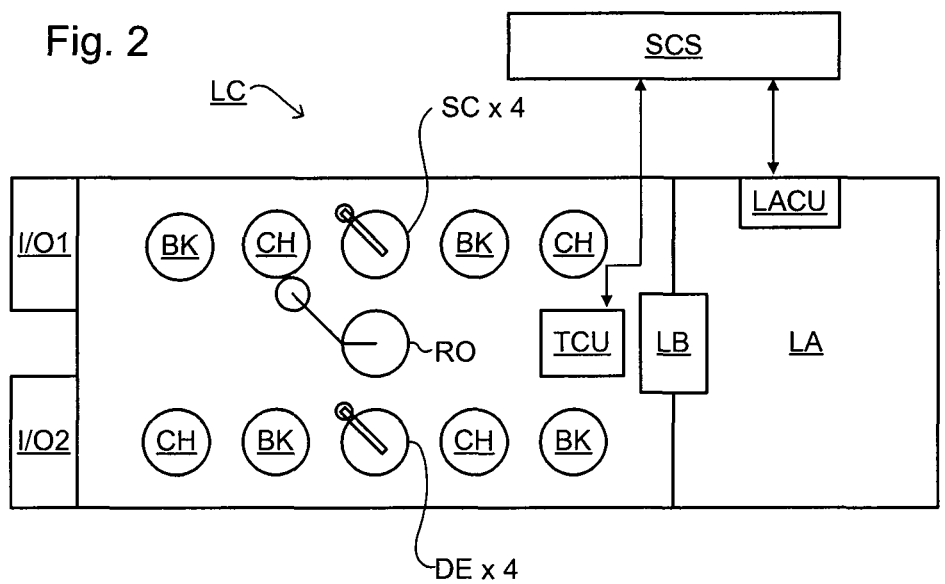
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers (e.g., coat), developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB), which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
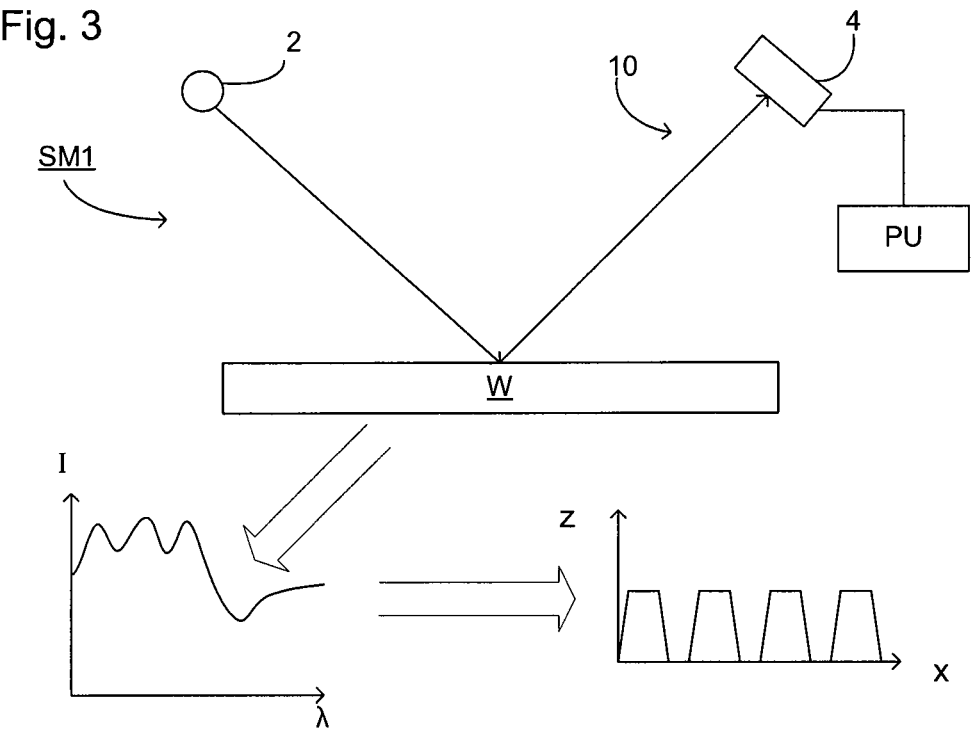
FIG. 3 depicts a first scatterometer.

FIG. 3 depicts a scatterometer SM1, which may be used in the present invention.

It comprises a broadband (white light) radiation projector 2, which projects radiation onto a substrate W. The reflected radiation is passed to a spectrometer detector 4, which detects (e.g., measures) a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression, or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
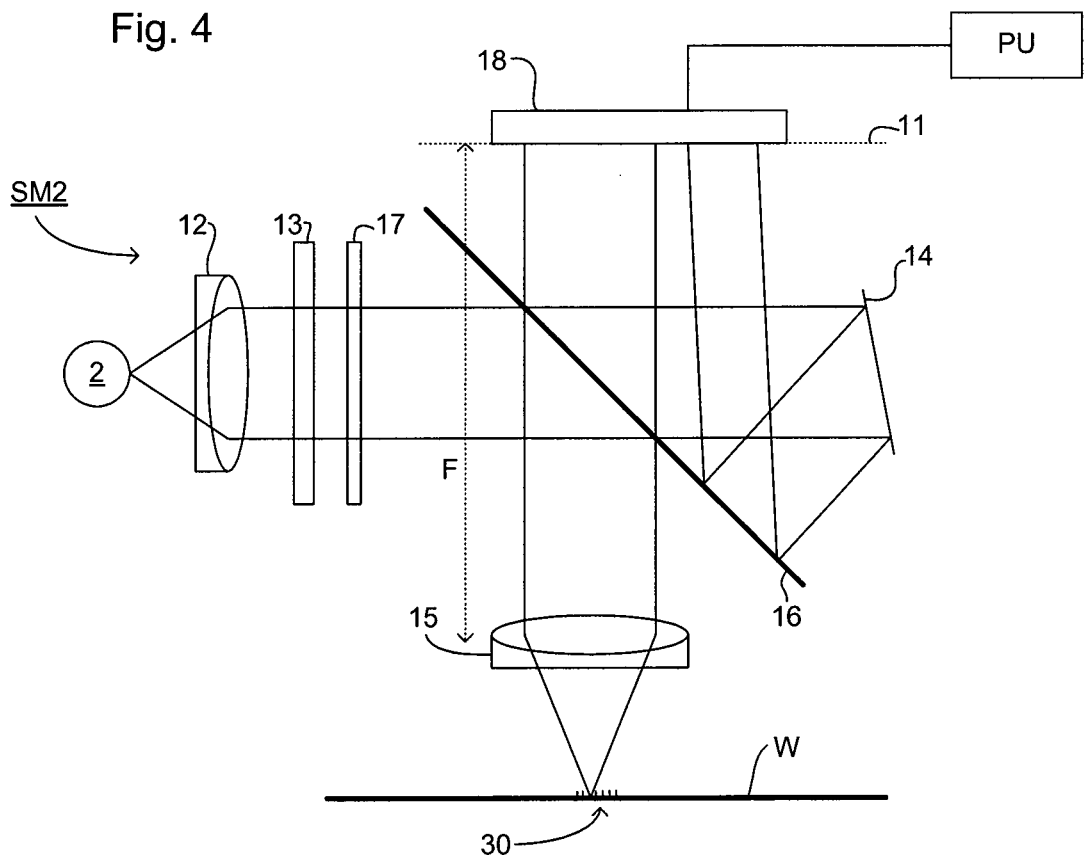
FIG. 4 depicts a second scatterometer.
Figure 5:
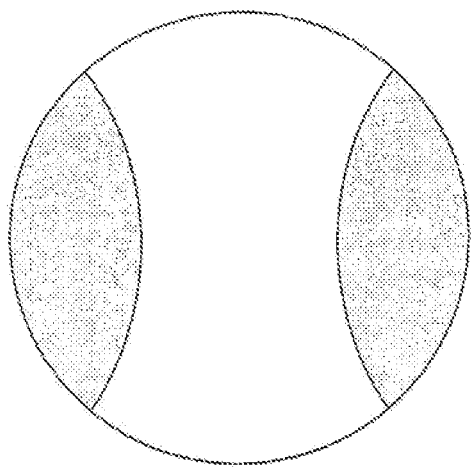
FIG. 5 depicts a pupil plane using conventional illumination.
Figure 6:
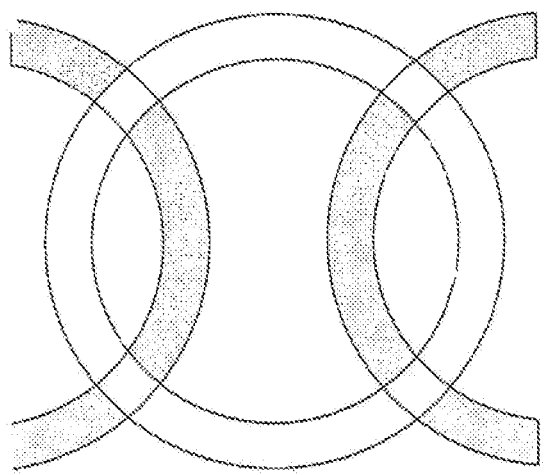
FIG. 6 depicts a pupil plane using angular illumination.

Another scatterometer SM2 that may be used with the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15. However, the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least $2\delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured, which increases metrology process robustness. This is described in more detail in EP1,628,164A, which is hereby incorporated by reference as background.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

According to the invention, the radiation beam illuminating the substrate during angular resolved spectrometry has an imaginary line. For any point (or area) in the illumination profile that is illuminated there is a corresponding point (or area) on the opposite side of the imaginary line which is not illuminated. Similarly, for any point in the illumination profile that is not illuminated, there is a corresponding point on the opposite side of the imaginary line that is illuminated. The simplest way of doing this is to illuminate half the illumination profile, as shown in FIG. 7a. The line of symmetry of the mark to be illuminated should be matched to, and parallel to the plane of symmetry of the illumination profile. The resulting pupil plane is shown in FIG. 7b. As can be seen, the first order diffraction pattern is depicted in one half and the zeroth order diffraction pattern is depicted in the other half of the pupil plane. The diffraction patterns are therefore separated, without any of the disadvantages associated with the use of an annular illumination profile. In this way, extra information from the first order is used without removing the information in the zeroth diffraction order. The characteristics of the mark can then be reconstructed using the separately measured zeroth and first diffraction orders measured using the method of the invention.

Another embodiment of the invention is depicted in FIG. 8. In this embodiment the illumination profile, shown in FIG. 8a is divided into four quadrants, with the first and third quadrants being illuminated and the second and fourth quadrants left unilluminated. Preferably, the quadrants are equal in size. There are thus two imaginary lines in this embodiment. This type of illumination profile is used in conjunction with marks having at least two degrees of symmetry that are aligned parallel to the imaginary lines of the illumination profile. The resulting pupil plane is shown in FIG. 8b.

Although FIG. 8a depicts an illumination profile with two of the four quadrants illuminated it is only necessary to illuminate one of the quadrants and such an illumination profile is depicted in FIG. 9a. The resulting pupil plane is depicted in FIG. 9b. Such an illumination profile is particularly useful in the illumination of, for example, an array of contact apertures. However, illuminating a second quadrant reduces the impact of sensor asymmetries. Moreover, it also gives more measured photos that help to improve the reproducibility of the measured mark characteristics.

Although this invention has been described in relation to zeroth and first order diffraction patterns, the same principle may be applied to first and second, and second and third order diffraction patterns. The illumination profile may be arranged such that they are separated, by, for example, using an illumination profile with only certain quadrants illuminated.

The measured angle-resolved spectrum contains separated zeroth and first diffraction order information that are both used in the reconstruction of the mark characteristics. Reconstruction methods may for example rely on real time regression methods, libraries or a mix of these two.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

Conclusion

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection apparatus configured to measure a property of a substrate, the apparatus comprising:
   an illumination system configured to provide a beam of radiation;
   a radiation projector configured to project the beam of radiation onto the substrate;
   a numerical aperture lens;
   a substrate comprising a mark with a line of symmetry that is parallel to and in alignment with a plane of symmetry of an illumination profile of the beam of radiation projected by the radiation projector, wherein the illumination profile comprises two quadrants spaced apart from each other, the two quadrants being substantially illuminated; and a detector configured to detect the radiation beam reflected from a surface of the substrate and separately detect a zeroth diffraction order and a higher diffraction order, wherein the illumination profile is such that at least one characteristic of the mark is reconstructed using the separately detected zeroth diffraction order and the higher diffraction order.

2. The apparatus of claim 1, wherein the higher diffraction order is the first diffraction order.

3. The apparatus of claim 1, wherein an intensity distribution of the beam of radiation is not symmetric about an imaginary line in a pupil plane and passing through an optical axis of the radiation projector.

4. The apparatus of claim 1, wherein the illumination profile is such that over at least a part of the illumination profile, portions on a first side of the imaginary line which are illuminated have corresponding portions symmetrically opposite on the other side of the imaginary line which are not illuminated, and at least a part of the portions on the first side of the imaginary line which are not illuminated have corresponding portions symmetrically opposite on the other side of the imaginary line which are illuminated.

5. The apparatus of claim 1, wherein the illumination system configures the radiation beam to have the illumination profile.

6. The apparatus of claim 1, wherein the illumination profile comprises a second imaginary line perpendicular to a first imaginary line, and over at least a part of the illumination profile, portions on a first side of the second imaginary line which are illuminated have corresponding portions symmetrically opposite on the other side of the second imaginary line which are not illuminated, and at least a part of the portions on the first side of the second imaginary line which are not illuminated have corresponding portions symmetrically opposite on the other side of the second imaginary line which are illuminated.

7. The apparatus of claim 1, wherein the two quadrants are equal in size.

8. The apparatus of claim 1, wherein the illumination profile has further comprises two non-illuminated quadrants.

9. The apparatus of claim 1, wherein the mark on the substrate comprises at least two degrees of symmetry that are in parallel and in alignment with respective imaginary lines of the illumination profile.

10. The apparatus of claim 1, wherein the illumination system is configured to block portions of the radiation corresponding to the areas in the pupil plane in which the first diffraction orders are detected.

11. A lithographic apparatus comprising:
an illumination optical system arranged to illuminate a pattern;
a projection optical system arranged to project an image of the pattern on to a substrate; and
an inspection apparatus configured to measure a property of a substrate, the apparatus comprising:
an illumination system configured to provide a beam of radiation;
a radiation projector configured to project the beam of radiation onto the substrate;
a numerical aperture lens;
a substrate comprising a mark with a line of symmetry that is in parallel and in alignment with a plane of symmetry of an illumination profile of the beam of radiation projected by the radiation projector,
wherein the illumination profile comprises two quadrants positioned opposite to each other, the two quadrants being substantially illuminated; and
a detector configured to detect the radiation beam reflected from a surface of the substrate and separately detect a zeroth diffraction order and a higher diffraction order,
wherein the illumination profile is such that at least one characteristic of the mark is reconstructed using the separately detected zeroth diffraction order and the higher diffraction order.

12. A lithographic cell comprising:
a coater arranged to coat substrates with a radiation sensitive layer;
a lithographic apparatus arranged to expose images onto the radiation sensitive layer of substrates coated by the coater;
a developer arranged to develop images exposed by the lithographic apparatus; and
an inspection apparatus configured to measure a property of a substrate, the apparatus comprising:
an illumination system configured to provide a beam of radiation;
a radiation projector configured to project the beam of radiation onto the substrate;
a numerical aperture lens;
a substrate comprising a mark with a line of symmetry that is in parallel and in alignment with a plane of symmetry of an illumination profile of the beam of radiation projected by the radiation projector,
wherein the illumination profile comprises two quadrants spaced apart from each other, the two quadrants being substantially illuminated; and
a detector configured to detect the radiation beam reflected from a surface of the substrate and separately detect a zeroth diffraction order and a higher diffraction order,
wherein the illumination profile is such that at least one characteristic of the mark is reconstructed using the separately detected zeroth diffraction order and the higher diffraction order.

13. A method of measuring a property of a substrate, the method comprising:
projecting a beam of radiation onto a target exposed on the substrate;
aligning a line of symmetry of a mark on the substrate in parallel with a plane of symmetry of an illumination profile of the projected beam of radiation;
detecting the radiation reflected by the substrate; and
determining the property from the reflecting radiation,
wherein:
the illumination profile comprises two quadrants spaced apart from each other, the two quadrants being substantially illuminated; and
the illumination profile of the beam of radiation projected by a radiation projector is such that an intensity distribution of the beam of radiation is not symmetric about an imaginary line in a pupil plane and passing through an optical axis of the radiation projector.

14. An inspection apparatus configured to measure a property of a substrate, the apparatus comprising:
an illumination system configured to provide a beam of radiation;
a radiation projector configured to project the radiation beam onto the substrate;
a numerical aperture lens;

a substrate comprising a mark with a line of symmetry that is in parallel and in alignment with a plane of symmetry of an illumination profile of the beam of radiation projected by the radiation projector, wherein the illumination profile comprises two quadrants spaced apart from each other, the two quadrants being substantially illuminated; and a detector configured to detect the radiation beam reflected from a surface of the substrate and to separately detect a zeroth and a first diffraction orders, wherein the illumination profile of the radiation beam projected by the radiation projector is such that an intensity distribution of the radiation beam is not symmetric about the an imaginary line in a pupil plane and passing through an optical axis of the radiation projector.

15. The apparatus according to claim 14, wherein the illumination profile is such that, over at least a part of the illumination profile, portions on a first side of the imaginary line that are illuminated have corresponding portions symmetrically opposite on the other side of the imaginary line that are not illuminated, and portions on the first side of the imaginary line that are not illuminated have corresponding portions symmetrically opposite on the other side of the imaginary line that are illuminated.

16. The apparatus according to claim 14, wherein the illumination system configures the radiation beam to have the illumination profile.

17. The apparatus according to claim 14, wherein the illumination profile as comprises a second imaginary line perpendicular to a first imaginary line, and wherein over at least a part of the illumination profile, portions on a first side of the second imaginary line that are illuminated have corresponding portions symmetrically opposite on the other side of the second imaginary line that are not illuminated, and portions on the first side of the second imaginary line that are not illuminated have corresponding portions symmetrically opposite on the other side of the second imaginary line that are illuminated.

18. The apparatus according to claim 14, wherein the two quadrants are equal in size.

19. The apparatus according to claim 14, wherein the two quadrants are positioned opposite to each other.

20. The apparatus of claim 14, wherein the illumination profile further comprises two non-illuminated quadrants.

21. The apparatus according to claim 20, wherein the two non-illuminated quadrants are equal in size.

22. The apparatus of claim 17, wherein the mark on the substrate comprises at least two degrees of symmetry that are in parallel and in alignment with respective imaginary lines of the illumination profile.

23. The apparatus of claim 14, wherein the illumination system is configured to block portions of the radiation beam corresponding to areas in the pupil plane in which the first diffraction orders are detected.

24. A lithographic apparatus comprising:
an illumination optical system arranged to illuminate a pattern;
a projection optical system arranged to project an image of the pattern on to a substrate; and
an inspection apparatus comprising:
a substrate comprising a mark with a line of symmetry that is in parallel and in alignment with a plane of symmetry of an illumination profile of a beam of radiation projected by a radiation projector,
wherein the illumination profile comprises two quadrants positioned opposite to each other, the two quadrants being substantially illuminated; and
a detector configured to detect the radiation beam reflected from a surface of the substrate and to separately detect a zeroth and a first diffraction orders,
wherein the illumination profile of the reflected radiation beam is such that an intensity distribution thereof is not symmetric about an imaginary line in a pupil plane and passing through an optical axis of the projection optical system.

25. A lithographic cell comprising:
a coater arranged to coat substrates with a radiation sensitive layer;
a lithographic apparatus arranged to expose images onto the radiation sensitive layer of substrates coated by the coater;
a developer arranged to develop images exposed by the lithographic apparatus; and
an inspection apparatus comprising:
a substrate comprising a mark with a line of symmetry that is in parallel and in alignment with a plane of symmetry of an illumination profile of a beam of radiation projected by a radiation projector,
wherein the illumination profile comprises two quadrants spaced apart from each other, the two quadrants being substantially illuminated; and
a detector configured to detect the radiation beam reflected from a surface of the substrate and to separately detect a zeroth and a first diffraction orders,
wherein the illumination profile of the reflected radiation beam is such that an intensity distribution thereof is not symmetric about an imaginary line in a pupil plane and passing through an optical axis of the projection optical system.

26. A method of measuring a property of a substrate, the method comprising:
projecting, with a projection optical system, a beam of radiation onto a target exposed onto the substrate;
aligning a line of symmetry of a mark on the substrate in parallel with a plane of symmetry of an illumination profile of the projected beam of radiation,
wherein the illumination profile comprises two quadrants spaced apart from each other, the two quadrants being substantially illuminated;
detecting radiation reflected by the substrate and separately detecting a zeroth diffraction order and a higher diffraction order; and
reconstructing at least one characteristic of the mark using the separately detected zeroth diffraction order and the higher diffraction order.

27. The method according to claim 26, wherein an intensity distribution of the beam of radiation is not symmetric about an imaginary line in a pupil plane and passing through an optical axis of the projection optical system.

* * * * *

UNITED STATES PATENT AND TRADEMARK OFFICE
CERTIFICATE OF CORRECTION

PATENT NO. : 8,705,007 B2  Page 1 of 1
APPLICATION NO. : 12/690221
DATED : April 22, 2014
INVENTOR(S) : Cramer et al.

It is certified that error appears in the above-identified patent and that said Letters Patent is hereby corrected as shown below:

In the Claims

In column 13, line 30, claim 17, please delete "as".

Signed and Sealed this
Second Day of September, 2014

Michelle K. Lee
*Deputy Director of the United States Patent and Trademark Office*